US008652140B2

(12) United States Patent
Neubardt et al.

(10) Patent No.: US 8,652,140 B2
(45) Date of Patent: Feb. 18, 2014

(54) DEVICE AND METHOD FOR OPERATING A TOOL RELATIVE TO BONE TISSUE AND DETECTING NEURAL ELEMENTS

(75) Inventors: Seth L Neubardt, White Plains, NY (US); William Keith Adcox, Memphis, TN (US); Sharonda Felton, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 51 days.

(21) Appl. No.: 13/342,454

(22) Filed: Jan. 3, 2012

(65) Prior Publication Data

US 2012/0109133 A1 May 3, 2012

Related U.S. Application Data

(63) Continuation of application No. 11/052,641, filed on Feb. 7, 2005, now Pat. No. 8,092,455.

(51) Int. Cl.
*A61B 17/88* (2006.01)
*A61B 17/16* (2006.01)

(52) U.S. Cl.
USPC .......................................................... 606/80

(58) Field of Classification Search
USPC .................. 606/79–85, 86 R, 104, 546, 554; 600/546, 554
See application file for complete search history.

(56) References Cited

U.S. PATENT DOCUMENTS

| | | |
|---|---|---|
| 2,704,064 A | 3/1955 | Fizzell et al. |
| 3,364,929 A | 1/1968 | Ide et al. |
| 3,664,329 A | 5/1972 | Naylor |
| 3,682,162 A | 8/1972 | Colyer |

(Continued)

FOREIGN PATENT DOCUMENTS

| | | |
|---|---|---|
| FR | 2865920 B1 | 2/2004 |
| WO | 0066217 A1 | 11/2000 |
| WO | 03/037170 A2 | 5/2003 |
| WO | 2004/066850 A1 | 8/2004 |

OTHER PUBLICATIONS

H.L. Journee et al., System for Intra-Operative Monitoring of the Cortical Integrety of the Pedicle During Pedicle Screw Placement in Low-Back Surgery: Design and Clinical Results, 18th Annual International Conference of the IEEE Engineering in Medicine and Biology Society, Amsterdam 1996. p. 144-145, 0-7803-3811-1/97,Copyright IEEE.

(Continued)

*Primary Examiner* — Kevin T Truong
*Assistant Examiner* — Christopher Beccia
(74) *Attorney, Agent, or Firm* — Sorell, Lenna & Schmidt LLP

(57) ABSTRACT

An apparatus for providing medical treatment includes a tool portion configured to operate relative to bone tissue, a handle portion to operate the tool portion, and a nerve monitoring system to detect neural elements. The tool portion includes an insulated shaft comprised of an electrically conductive member and a non-insulated tip. The shaft carries an electrical signal to the non-insulated tip. The handle portion, which is removably and operably connected to the tool portion, incorporates an operating system to rotationally operate the tool portion. Additionally, the nerve monitoring system is linked to the tip and is operable to detect a neural element as a function of a characteristic of the electrical signal on the tip. Upon detection of a neural element, the nerve monitoring system provides a signal to the operating system of the handle portion directing the operating system stop rotation of the tool portion.

5 Claims, 4 Drawing Sheets

(56) References Cited

U.S. PATENT DOCUMENTS

| | | | |
|---|---|---|---|
| 3,811,449 A | 5/1974 | Gravlee et al. | |
| 3,830,226 A | 8/1974 | Staub et al. | |
| 3,892,232 A | 7/1975 | Neufeld | |
| 3,957,036 A | 5/1976 | Normann | |
| 4,099,519 A | 7/1978 | Warren | |
| 4,207,897 A | 6/1980 | Lloyd et al. | |
| 4,224,949 A | 9/1980 | Scott et al. | |
| 4,235,242 A | 11/1980 | Howson et al. | |
| 4,285,347 A | 8/1981 | Hess | |
| 4,515,168 A | 5/1985 | Chester et al. | |
| 4,519,403 A | 5/1985 | Dickhudt | |
| 4,545,374 A | 10/1985 | Jacobson | |
| 4,573,448 A | 3/1986 | Kambin | |
| 4,592,369 A | 6/1986 | Davis et al. | |
| 4,633,889 A | 1/1987 | Talalla et al. | |
| 4,650,375 A | 3/1987 | Millsap | |
| 4,658,835 A | 4/1987 | Pohndorf | |
| 4,759,377 A | 7/1988 | Dykstra | |
| 4,803,976 A | 2/1989 | Frigg et al. | |
| 4,807,642 A | 2/1989 | Brown | |
| 4,823,791 A | 4/1989 | D'Amelio et al. | |
| 4,892,105 A | 1/1990 | Prass | |
| 4,926,865 A | 5/1990 | Oman | |
| 4,962,766 A | 10/1990 | Herzon | |
| 4,964,411 A | 10/1990 | Johnson et al. | |
| 4,965,909 A | 10/1990 | McCullough et al. | |
| 4,974,595 A | 12/1990 | Nordenstrom | |
| 5,007,902 A | 4/1991 | Witt | |
| 5,058,602 A | 10/1991 | Brody | |
| 5,081,990 A | 1/1992 | Deletis | |
| 5,092,344 A | 3/1992 | Lee | |
| 5,127,403 A | 7/1992 | Brownlee | |
| 5,161,533 A | 11/1992 | Prass et al. | |
| 5,196,015 A | 3/1993 | Neubardt | |
| 5,204,598 A | 4/1993 | Torii et al. | |
| RE34,390 E | 9/1993 | Culver | |
| 5,242,443 A | 9/1993 | Kambin | |
| 5,255,691 A | 10/1993 | Otten | |
| 5,282,468 A | 2/1994 | Klepinski | |
| 5,284,153 A | 2/1994 | Raymond et al. | |
| 5,284,154 A | 2/1994 | Raymond et al. | |
| 5,313,956 A | 5/1994 | Knutsson et al. | |
| 5,375,067 A | 12/1994 | Berchin | |
| 5,433,739 A | 7/1995 | Sluijter et al. | |
| 5,474,558 A | 12/1995 | Neubardt | |
| 5,480,440 A | 1/1996 | Kambin | |
| 5,482,038 A | 1/1996 | Ruff | |
| 5,540,235 A | 7/1996 | Wilson | |
| 5,560,372 A | 10/1996 | Cory | |
| 5,566,678 A | 10/1996 | Cadwell | |
| 5,579,781 A | 12/1996 | Cooke | |
| 5,593,429 A | 1/1997 | Ruff | |
| 5,630,813 A | 5/1997 | Kieturakis | |
| 5,671,752 A | 9/1997 | Sinderby et al. | |
| 5,711,307 A | 1/1998 | Smits | |
| 5,775,331 A | 7/1998 | Raymond et al. | |
| 5,779,642 A | 7/1998 | Nightengale | |
| 5,797,854 A | 8/1998 | Hedgecock | |
| 5,807,275 A | 9/1998 | Jamshidi | |
| 5,830,151 A | 11/1998 | Hadzic et al. | |
| 5,851,191 A | 12/1998 | Gozani | |
| 5,853,373 A | 12/1998 | Griffith et al. | |
| 5,876,405 A | 3/1999 | Del Rio et al. | |
| 5,885,219 A | 3/1999 | Nightengale | |
| 5,888,196 A | 3/1999 | Bonutti | |
| 5,902,105 A | 5/1999 | Uejima et al. | |
| 5,928,158 A | 7/1999 | Aristides | |
| 5,976,094 A | 11/1999 | Gozani | |
| 6,004,262 A | 12/1999 | Putz et al. | |
| 6,038,477 A | 3/2000 | Kayyali | |
| 6,050,992 A | 4/2000 | Nichols | |
| 6,081,741 A | 6/2000 | Hollis | |
| 6,104,960 A | 8/2000 | Duysens et al. | |
| 6,132,386 A | 10/2000 | Gozani et al. | |
| 6,132,387 A | 10/2000 | Gozani et al. | |
| 6,146,335 A | 11/2000 | Gozani | |
| 6,159,179 A | 12/2000 | Simonson | |
| 6,161,047 A | 12/2000 | King et al. | |
| 6,224,549 B1 | 5/2001 | Drongelen | |
| 6,259,945 B1 | 7/2001 | Epstein et al. | |
| 6,261,307 B1 | 7/2001 | Yoon et al. | |
| 6,266,558 B1 | 7/2001 | Gozani et al. | |
| 6,277,094 B1 | 8/2001 | Schendel | |
| 6,283,960 B1 | 9/2001 | Ashley | |
| 6,312,392 B1 | 11/2001 | Herzon | |
| 6,391,005 B1 | 5/2002 | Lum et al. | |
| 6,466,817 B1 | 10/2002 | Kaula et al. | |
| 6,500,128 B2 | 12/2002 | Marino | |
| 6,512,958 B1 | 1/2003 | Swoyer et al. | |
| 6,514,258 B1 | 2/2003 | Brown et al. | |
| 6,535,759 B1 | 3/2003 | Epstein et al. | |
| 6,554,778 B1 | 4/2003 | Fleming, III | |
| 6,562,046 B2 | 5/2003 | Sasso | |
| 6,564,078 B1 | 5/2003 | Marino et al. | |
| 6,579,244 B2 | 6/2003 | Goodwin | |
| 6,582,441 B1 | 6/2003 | He et al. | |
| 6,605,085 B1 | 8/2003 | Edwards | |
| 6,638,281 B2 | 10/2003 | Gorek | |
| 6,796,985 B2 | 9/2004 | Bolger et al. | |
| 7,050,848 B2 | 5/2006 | Hoey et al. | |
| 7,079,883 B2 | 7/2006 | Marino et al. | |
| 7,177,677 B2 | 2/2007 | Kaula et al. | |
| 2002/0072686 A1 | 6/2002 | Hoey et al. | |
| 2002/0147485 A1 | 10/2002 | Mamo et al. | |
| 2003/0028146 A1 | 2/2003 | Aves | |
| 2003/0045808 A1 | 3/2003 | Kaula et al. | |
| 2003/0083688 A1 | 5/2003 | Simonson | |
| 2003/0105503 A1 | 6/2003 | Marino | |
| 2003/0181958 A1 | 9/2003 | Dobak, III | |
| 2003/0187348 A1 | 10/2003 | Goodwin | |
| 2003/0195405 A1 | 10/2003 | Marino et al. | |
| 2004/0040727 A1 | 3/2004 | Miller | |
| 2004/0102783 A1 | 5/2004 | Sutterlin et al. | |
| 2004/0122482 A1 | 6/2004 | Tung et al. | |
| 2004/0225228 A1 | 11/2004 | Ferree | |
| 2005/0075578 A1 | 4/2005 | Gharib et al. | |
| 2005/0131415 A1 | 6/2005 | Hearn et al. | |
| 2005/0149053 A1 | 7/2005 | Varieur et al. | |
| 2006/0173374 A1 | 8/2006 | Neubardt et al. | |
| 2006/0173521 A1 | 8/2006 | Pond, Jr. et al. | |
| 2006/0178594 A1 | 8/2006 | Neubardt et al. | |
| 2006/0200023 A1 | 9/2006 | Melkent et al. | |

OTHER PUBLICATIONS

International Search Report, mailed Jun. 21, 2006, in PCT/US2006/004246.

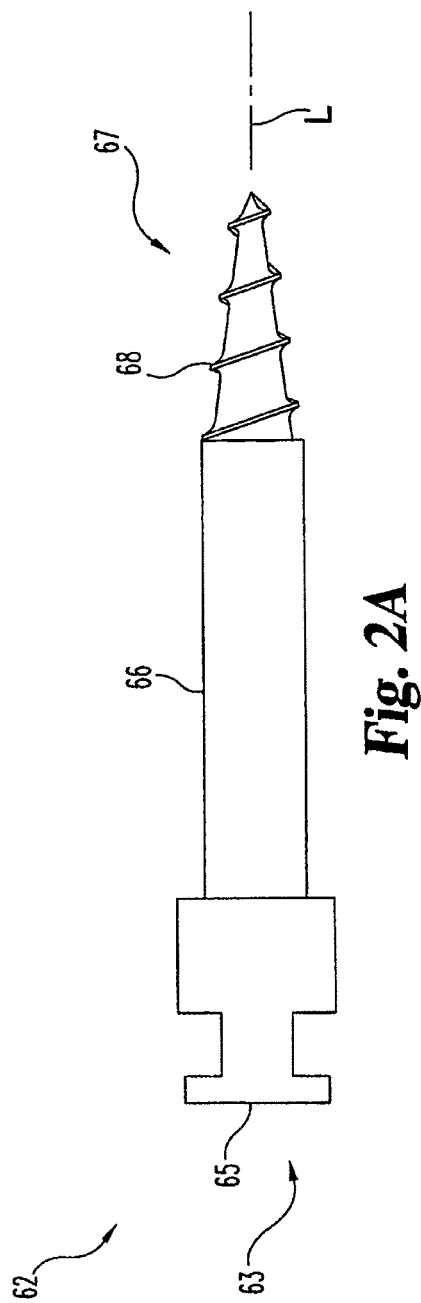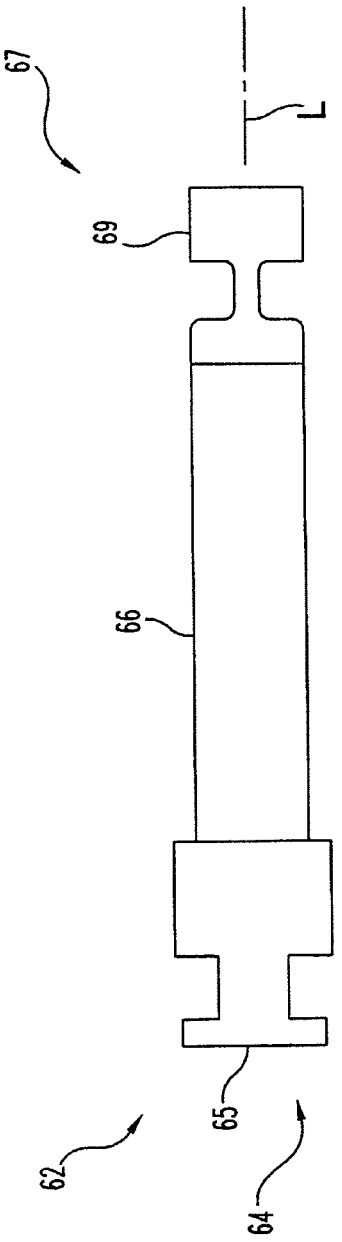
Fig. 2A
Fig. 2B

DEVICE AND METHOD FOR OPERATING A TOOL RELATIVE TO BONE TISSUE AND DETECTING NEURAL ELEMENTS

This application is a continuation of co-pending U.S. patent application Ser. No. 11/052,641, filed Feb. 7, 2005, which is incorporated herein by reference.

BACKGROUND

Surgery for a patient can be painful and traumatic, particularly in the affected area of the patient's body. To accomplish spinal fixation, a necessary procedure often involves forming a hole in a pedicle wall of a vertebra in a patient's spine and inserting a spinal pedicle screw into the hole. Pedicle screws are advantageous in that they are strong and provide stability, however, care must be taken to avoid nerve impingement during formation of the holes and the placement of pedicle screws in the spine. Measures taken to simultaneously monitor and locate any neural elements can facilitate hole formation and screw insertion.

Locating defects such as openings in bone tissue that expose nerves can be difficult. Some procedures involve monitoring muscle reactions to electrical stimulation to locate nerves in an area of bone tissue. If a nerve is not located and a screw contacts an exposed nerve, the screw can impinge on the nerve or become too close to the nerve root causing pain and other implications for the patient. Locating neural elements during the hole formation and screw insertion processes can facilitate such surgical procedures.

There remains a need for instruments and methods that can be employed for locating neural elements during formation of a hole in the pedicle wall and/or insertion of a screw therein. The present invention is directed to meeting these needs, among others.

SUMMARY

According to one aspect, an apparatus is provided comprising a tool portion configured to operate relative to bone tissue, a handle portion to operate the tool portion, and a nerve monitoring system to detect neural elements. The tool portion includes an insulated shaft comprised of an electrically conductive member and a non-insulated tip. The shaft carries an electrical signal to the non-insulated tip. The handle portion, which is removably and operably connected to the tool portion, incorporates an operating system to operate the tool portion. Additionally, the nerve monitoring system is connected to the handle portion and is operable to detect a neural element as a function of a characteristic of the electrical signal at the tip. Upon detection of a neural element, the nerve monitoring system provides a signal to the operating system of the handle portion directing the operating system to change an operative mode of the tool portion.

Another aspect involves an apparatus comprising a tool portion configured to operate relative to bone tissue and a handle portion removably and operably coupled to the tool portion including a system for rotating the tool portion. The tool portion includes an elongated insulated shaft and a non-insulated tip at a distal end of the shaft. The shaft is comprised of an electrically conductive member. The operating system in the handle portion is operable to change an operative mode of the tool portion in response to the detection of neural elements via an electrical signal at the tip of the tool portion.

Yet another aspect involves a method comprising providing a handle portion, which incorporates an operating system, and connecting a tool portion to the handle portion. The tool portion includes an insulated shaft and a non-insulated tip. Additionally, the operating system is operable to rotate the tool portion about a longitudinal axis. The method further comprises providing a nerve monitoring system operably connected to the handle portion, providing an electrical signal to the tip, and rotating the tool portion relative to bone tissue. The nerve monitoring system provides an indication of the detection of a neural element as a function of the electrical signal. Upon detection of the neural element in the bone tissue, the nerve monitoring system sends a signal to the operating system of the handle portion to stop rotation of the tool portion.

Another aspect involves a system comprising a tool portion, a handle portion, and a nerve monitoring system. The tool portion includes an insulated shaft extending along a longitudinal axis and a non-insulated tip. The handle portion is operably and rotatably coupled to the tool portion and configured to rotate the tool portion relative to the handle portion. The nerve monitoring system is electrically coupled to the tool portion to provide an electrical signal to the tip to detect neural elements proximate the tip of the tool portion.

BRIEF DESCRIPTION OF THE DRAWINGS

FIG. 2A is a schematic view of one embodiment attachment to a handle device.

FIG. 2B is a schematic view of another embodiment tool attachment to a handle device.

DETAILED DESCRIPTION

Figure 1:
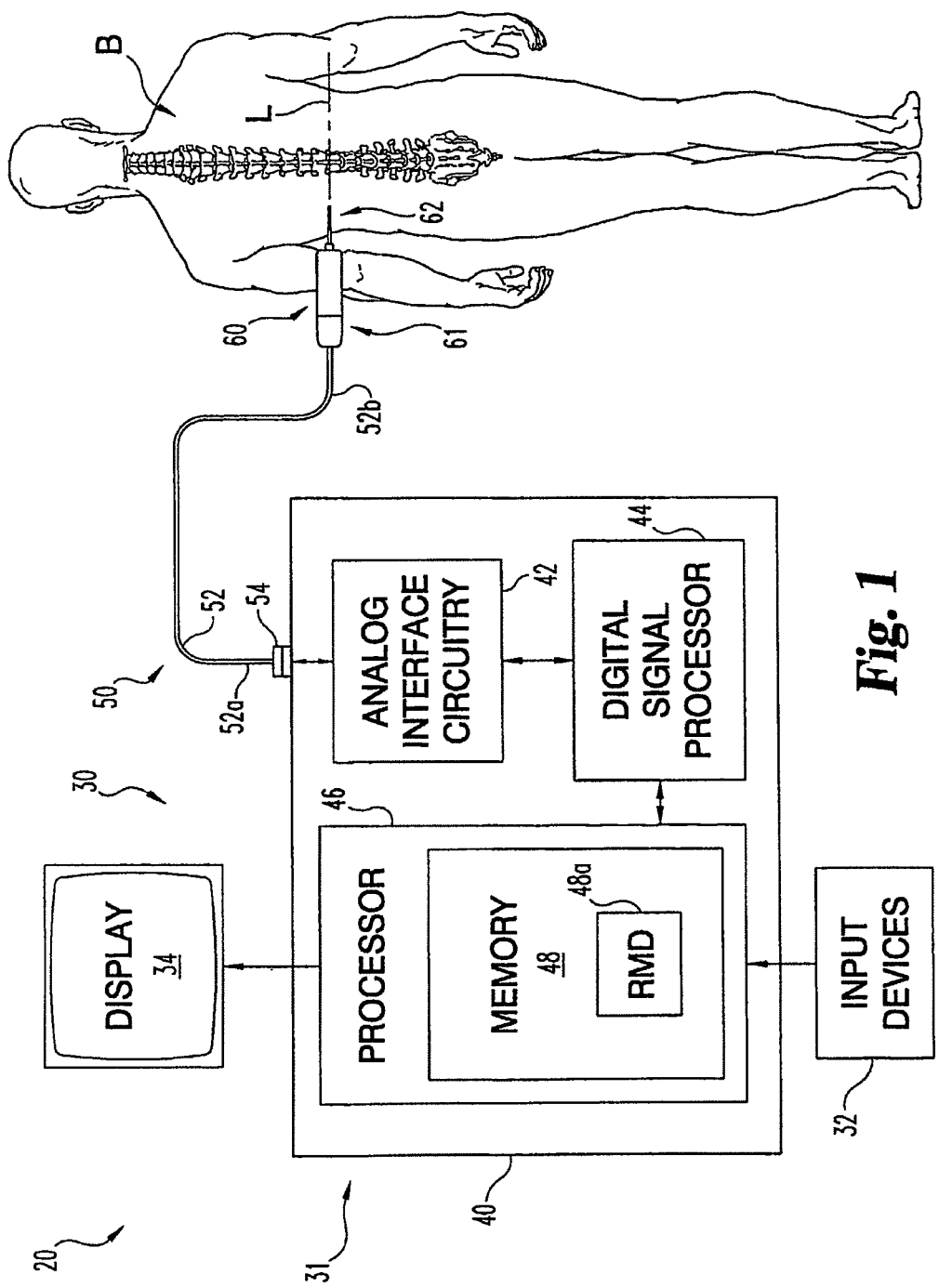
FIG. 1 is a schematic view of a medical system.

For the purposes of promoting an understanding of the principles of the invention, reference will now be made to the embodiments illustrated in the drawings and specific language will be used to describe the same. It will nevertheless be understood that no limitation of the scope of the invention is hereby intended, such alterations and further modifications in the illustrated devices, and such further applications of the principles of the invention as illustrated herein being contemplated as would normally occur to one skilled in the art to which the invention relates.

An apparatus for providing medical treatment includes a tool portion configured to operate relative to bone tissue, a handle portion to operate the tool portion, and a nerve monitoring system to detect neural elements. The tool portion includes an insulated shaft comprised of an electrically conductive member and a non-insulated tip. The shaft carries an electrical signal to the non-insulated tip. The handle portion, which is removably and operably connected to the tool portion, incorporates an operating system to operate the tool portion. Additionally, the nerve monitoring system is connected to the handle portion and is operable to detect a neural element as a function of a characteristic of the electrical signal in the tip. Upon detection of a neural element, the nerve monitoring system provides a signal to the operating system of the handle portion directing the operating system to change an operative mode of the tool portion.

FIG. 1 illustrates system 20 that includes a medical device and associated equipment arranged to provide medical treatment. System 20 is arranged to create holes and insert bone screws in a pedicle wall of one or more vertebrae of spinal column B. Further, system 20 is arranged to provide nerve monitoring and change an operative mode of the device creating the hole or inserting the screw upon detection of a neural element. The change in operative mode can include stopping rotation of the tool portion and/or reversing rotation of the tool portion and allow for removal of the device from the bone tissue upon detection of a neural element.

System 20 includes nerve monitoring system 30, connection link 50, and medical device 60. Device 60 extends generally along a longitudinal axis L and includes a handle portion 61 and a tool portion 62. Nerve monitoring system 30 includes equipment 31 coupled to device 60 with connection link 50 or integrated with device 60. Device 60 is configured for operation relative to a spinal pedicle wall of spinal column B of a human patient or subject, as schematically represented in FIG. 1. One example of a suitable system 30 is the NIM-Spine® System marketed by Medtronic, Inc.

Equipment 31 may include operator input devices 32, operator display device 34, and various other operator-utilized equipment of system 20 that is external to a patient during use. Input devices 32 may include an alphanumeric keyboard and mouse or other pointing device of a standard variety. Alternatively or additionally, one or more other input devices can be utilized, such as a voice input subsystem or a different type as would occur to those skilled in the art. Operator display device 34 can be of a Cathode Ray Tube (CRT) type, Liquid Crystal Display (LCD) type, plasma type, Organic Light Emitting Diode (OLED) type, or such different type as would occur to those skilled in the art. Alternatively or additionally, one or more other operator output devices can be utilized, such as a printer, one or more loudspeakers, headphones, or such different type as would occur to those skilled in the art. Nerve monitoring system 30 also can include one or more communication interfaces suitable for connection to a computer network, such as a Local Area Network (LAN), Municipal Area Network (MAN), and/or Wide Area Network (WAN) like the Internet; a medical diagnostic device; another therapeutic device; a medical imaging device; a Personal Digital Assistant (PDA) device; a digital still image or video camera; and/or audio device, to name only a few. Nerve monitoring system 30 can be arranged to show other information under control of the operator.

Equipment 31 may also include processing subsystem 40 for processing signals and data associated with system 20. Subsystem 40 may include analog interface circuitry 42, Digital Signal Processor (DSP) 44, data processor 46, and memory 48. Analog interface circuitry 42 can be responsive to control signals from DSP 44 to provide corresponding analog stimulus signals to device 60. At least one of analog interface circuitry 42 and DSP 44 may include one or more digital-to-analog converters (DAC) and one or more analog-to-digital converters (ADC) to facilitate operation of system 20 in the manner to be described in greater detail hereinafter. Processor 46 can be coupled to DSP 44 to bidirectionally communicate therewith, selectively provide output to display device 34, and selectively respond to input from operator input devices 32.

DSP 44 and/or processor 46 can be of a programmable type; a dedicated, hardwired state machine; or a combination of these. DSP 44 and processor 46 perform in accordance with operating logic that can be defined by software programming instructions, firmware, dedicated hardware, a combination of these, or in a different manner as would occur to those skilled in the art. For a programmable form of DSP 44 or processor 46, at least a portion of this operating logic can be defined by instructions stored in memory 48. Programming of DSP 44 and/or processor 46 can be of a standard, static type; an adaptive type provided by neural networking, expert-assisted learning, fuzzy logic, or the like; or a combination of these.

Memory 48 is illustrated in association with processor 46; however, memory 48 can be separate from or at least partially included in one or more of DSP 44 and processor 46. Memory 48 includes at least one Removable Memory Device (RMD) 48a. Memory 48 can be of a solid-state variety, electromagnetic variety, optical variety, or a combination of these forms. Furthermore, memory 48 can be volatile, nonvolatile, or a mixture of these types. Memory 48 can be at least partially integrated with circuitry 42, DSP 44, and/or processor 46. RMD 48a can be a floppy disc, cartridge, or tape form of removable electromagnetic recording media; an optical disc, such as a CD or DVD type; an electrically reprogrammable solid-state type of nonvolatile memory, and/or such different variety as would occur to those skilled in the art. In still other embodiments, RMD 48a is absent.

Circuitry 42, DSP 44, and processor 46 can be comprised of one or more components of any type suitable to operate as described herein. Further, it should be appreciated that all or any portion of circuitry 42, DSP 44, and processor 46 can be integrated together in a common device, and/or provided as multiple processing units. For a multiple processing unit form of DSP 44 or processor 46; distributed, pipelined, and/or parallel processing can be utilized as appropriate. In one embodiment, circuitry 42 is provided as one or more components coupled to a dedicated integrated circuit form of DSP 44; processor 46 is provided in the form of one or more general purpose central processing units that interface with DSP 44 over a standard bus connection; and memory 48 includes dedicated memory circuitry integrated within DSP 44 and processor 46, and one or more external memory components including a removable disk form of RMD 48a. Circuitry 42, DSP 44, and/or processor 46 can include one or more signal filters, limiters, oscillators, format converters (such as DACs or ADCs), power supplies, or other signal operators or conditioners as appropriate to operate system 20 in the manner to be described in greater detail hereinafter.

In one embodiment, connection link 50 includes a link 52 in the form of a flexible cable with a proximal end 52a and an opposite distal end 52b. A connector 54 is electrically connected to equipment 31 of nerve monitoring system 30. Link 52 extends from connector 54 at proximal end 52a to distal end 52b where it is connected with device 60. Connection link 50 may include forms in addition to or in alternative to link 52, including one or more wires, cords, wireless links, infrared components, bluetooth, or other communication link. Further, it should be appreciated that other components, devices, and systems can be integrated into system 20, such as an endoscope system, a catheterization system, an imaging system, a lighting system, and/or a video camera system, to name a few examples. Connection link 50 and device 60 are movable toward and away from spinal column B in a surgical procedure that may include one or more of retractors, tubes, sleeves, guards, micro-incisions or other components not shown to enhance clarity.

Figure 3:
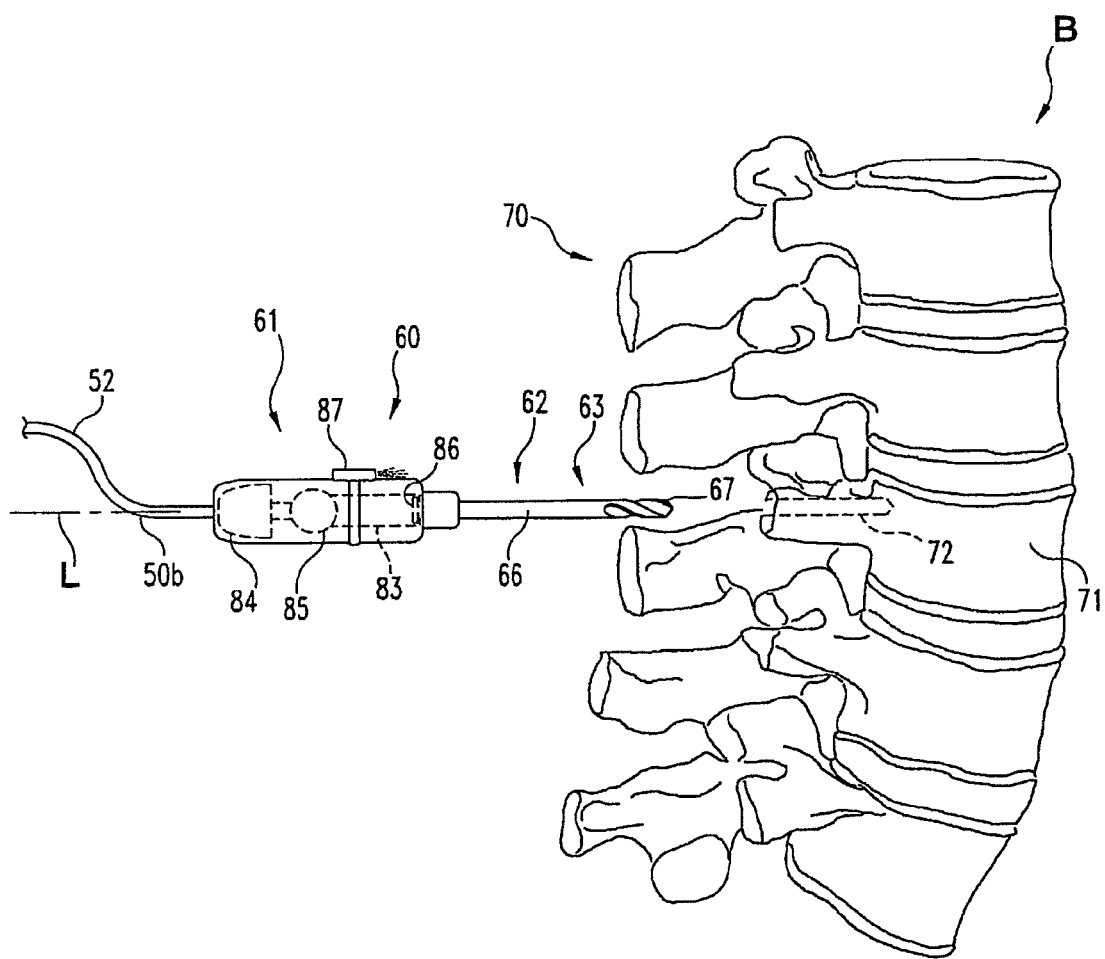
FIG. 3 is a partial, schematic view of a tool and handle device relative to a section of a spine.

In FIGS. 1 and 3, tool portion 62 includes a configuration suitable for use as a drill to cut and remove bone material to form a hole to receive a bone anchor. FIGS. 2A and 2B illustrate views of alternate embodiments of the components of tool portion 62. As examples, tool portion 62 can be a tap 63 (FIG. 2A) or a screw driver 64 (FIG. 2B.) Each tool portion 62 generally includes a universal connector 65 at its proximal end, a shaft 66, and a non-insulated tip 67 at a distal end. Universal connector 65 may include any suitable configuration for releasable connection with handle portion 61. In the illustrated embodiment, tap 63 includes a tapping head 68 at a distal end thereof configured to form a tapped hole pattern to receive a threaded portion of a bone anchor. Screw driver 64 includes driver head 69 at a distal end thereof that may include any suitable configuration for positioning in or about a screw, bolt or other device to be implanted in the pedicle with application of rotary force.

It should be appreciated that tip 67 can be other any other dissection or resection tool that performs a function relative to spinal column B. In the illustrated embodiment, tool portion 62 is generally cylindrically shaped about longitudinal axis L. Universal connector 65 and shaft 66 are composed of an electrically conductive material with an insulative member or coating thereabout to prevent shunting of electricity delivered therethrough to adjacent tissue or devices. Tip 67 is not insulated so that it is exposed to the adjacent bone tissue and carries an electrical signal for detection of nerve proximity.

FIG. 3 illustrates the components of one embodiment of device 60 and the relationship of device 60 to a vertebra 71 in segment 70 of spinal column B. Handle portion 61 is generally cylindrically shaped and elongated about longitudinal axis L. Handle portion 61 generally includes an operating system or set of operating equipment to perform functions during the operation of system 20. Handle portion 61 is composed of an insulative member or coating surrounding an electrically conductive shaft 83. The insulative member or coating thereabout allows handling of handle portion 61 and prevents shunting of electricity delivered therethrough to adjacent tissue or devices.

In one embodiment, handle portion 61 carries a circuit 84 and a motor 85 which operates to rotate shaft 83 and tool portion 62 coupled thereto about longitudinal axis L. Shaft 83 includes a rotatable coupling member 86 at a distal end thereof to operably connect with universal connector 65 of tool portion 62. It should be appreciated that handle portion 61 and tool portion 62 can be operably, rotatably, and electrically coupled together by any appropriate means, including interference fits, fasteners, chucks, and ball-detent mechanisms, for example. Additionally, handle portion 61 can be operable to provide an indication when tool portion 62 is coupled thereto. Device 60 can further include a light assembly 87 to illuminate an area of bone tissue of vertebra 71 or provide light to hole 72 in bone tissue of vertebra 71. Light assembly 87 can include a removable clip-on type element, or can be formed as an integral unit with handle portion 61.

Tool portion 62 can be provided in electrical engagement with a source for an electrical signal to locate neural elements proximate tool portion 62. For example, an electrical lead can extend from tool portion 62, through handle portion 61, to nerve monitoring system 30 for coupling with a source of electrical current either separately from or as a part of connection link 50. The electrical current is delivered to tip 67 to allow monitoring and detection of neural elements based on the proximity and response of the neural elements to the electrical signal. In the embodiment illustrated in FIG. 3, tool portion 62 is a drill configured for creation of hole 72 during use. During creation of hole 72, tip 67 carries an electrical signal that provides an indication of the proximity of neural elements in the bone tissue relative to the tip 67 during formation of the hole 72. Other embodiments contemplate tool portions that allow detection of nerve proximity during tapping of hole 72 and during insertion of an anchor into hole 72. One example of a surgical probe and procedure for detecting neural elements is provided in U.S. Pat. No. 5,474,558 to Neubardt, which is incorporated herein by reference in its entirety.

Figure 4A:
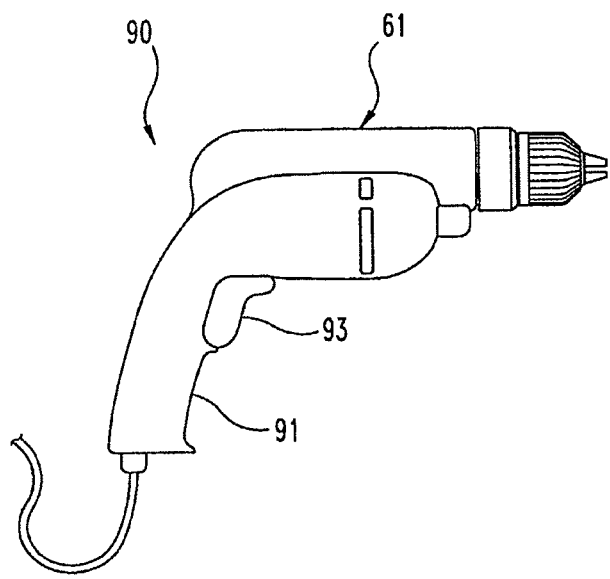
FIG. 4A is a schematic view of another embodiment handle device.
Figure 4B:
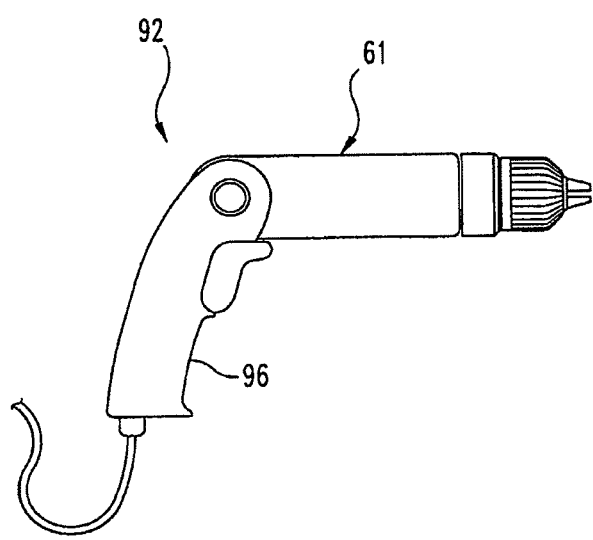
FIG. 4B is a schematic view of another embodiment handle device

In FIG. 2 handle portion 61 is shown in cylindrical form. FIGS. 4A and 4B illustrate alternative handle configurations for use with handle portion 61. For example, handle 90 is provided with a pistol grip portion 91 that removably receives or is integrally formed with handle portion 91. Pistol grip portion 91 includes a trigger 93 operable coupled to handle portion 61 that facilitates user to control operation of tool portion 62 and facilitates positioning and maintaining handle portion 61 in the desired position during the surgical procedure. In FIG. 4B, handle 92 includes a pistol grip configuration with a pistol grip portion 96 pivotally coupled to handle portion 61. The pivotal connection allows a change of attitude of handle portion 61 relative to the gripping portion 96 and facilitates control and repositioning of the instrument during the surgical procedure as may be needed to accommodate the surgical approach, tool portions, and instruments employed with handle portion 61.

Generally referring to FIGS. 1-4, the operation of system 20 includes attaching a selected tool portion 62 to handle portion 61 by engaging universal connector 65 with coupling member 86 of handle portion 61. Surgical access is provided to an area of bone tissue which, in one embodiment, is an area of tissue within a spinal pedicle wall of vertebra 71 of spinal segment 70. Nerve monitoring system 30 provides an electrical signal to tip 67 of tool portion 62. Circuit 84 and motor 85 are operable to rotate tool portion 62 about longitudinal axis L. In one embodiment, the rotation of tool portion 62 occurs at a relatively low speed with a relatively high torque to facilitate removal of bone tissue while preventing rapid advancement of the tool portion into the bone tissue during formation, tapping or anchor insertion relative to hole 72.

In one embodiment, the electric signal in tip 67 provides electrical stimulation to the tissue surrounding hole 72, and the patient response to the nerve stimulation is monitored to determine whether a neural element threshold has been reached. The threshold can correspond to, for example, an indication of the presence a neural element and its proximity relative to tip 67. In another embodiment, when tip 67 is positioned near or proximate a neural element, in certain situations, the presence of the neural element creates an electrical current path for the signal carried by tip 67. The current path provides an indication to nerve monitoring system 30 of the presence of the neural element, and corrective action can then be taken by the surgeon based on this indication. In other words, detection of the neural element threshold occurs as a function of the electrical signal at tip 67 inducing a reaction in the patient or particular reading at the threshold. The threshold causes a signal from the nerve monitoring system 30 to device 60 that changes an operative mode of device 60.

In one embodiment, upon detection of a neural element within a predetermined proximity of tip 67, nerve monitoring system 30 is operable send a signal to circuit 84 that stops operation of motor 85 in handle portion 61, stopping rotation of tool portion 62. Thus, system 20 operates to automatically stop rotation and operation of tool portion 62 to prevent further advancement of the tool portion or anchor into the bone tissue. In another embodiment, upon receipt of the stop signal circuit 84 functions to automatically reverse the direction of rotation of tool portion 62 to facilitate withdrawal of or backing up of tool portion 62 from the bone tissue. If no neural element is detected, the operation of tool portion 62 continues until successful completion of hole formation and/or bone screw insertion.

In one embodiment, tool portion 62 is autoclavable for re-use after a particular use. In another embodiment, tool portion 62 is disposable after each use, and a different tool portion 62 is inserted into handle portion 61 for further operation of system 20. In still another embodiment, the entire device 60 is disposable. In an another embodiment, nerve monitoring system 30 is absent from system 20 and an operating system within handle portion 61 is operable to detect neural elements and provide signals to circuit 84 to stop operation of tool portion 62. It should be appreciated that other steps or stages can be incorporated into the operating procedure of system 20, or the steps of operation of system 20 can be arranged differently in order to complete the surgical procedure.

While the invention has been illustrated and described in detail in the drawings and foregoing description, the same is to be considered as illustrative and not restrictive in character. All changes and modifications that come within the spirit of the invention are desired to be protected.

What is claimed is:

1. A surgical method, comprising:
   providing a handle portion incorporating an operating system;
   connecting a tool portion to the handle portion, wherein the tool portion includes an insulated shaft and non-insulated tip, and wherein the handle portion is configured to electrically insulate a user of the tool portion from an electrical signal induced at the tip; wherein the operating system is operable to rotate the tool portion about a longitudinal axis thereof;
   operably connecting a nerve monitoring system to the tool portion;
   providing an electrical signal to the tip and into a patient;
   rotating the tool portion relative to bone tissue of the patient;
   detecting a neural element threshold of a neural element of the patient as a function of the electrical signal, wherein the detecting is performed by the nerve monitoring system; the detection based on at least one of:
      monitoring a muscle reaction of the patient to the electrical signal interacting with a nerve; and
      a detected increase in electrical current flowing through the tip;
   stopping rotation of the tool portion upon detection of the neural element threshold to protect the neural element of the patient; wherein the stopping rotation is a result of a signal sent to the operating system in the handle portion from the nerve monitoring system.

2. The method of claim 1 wherein the operating system includes circuitry and a motor operable to rotate the tool portion about the longitudinal axis.

3. The method of claim 1 wherein the tool portion is selected from the group consisting of: a drill, a tap and a driver.

4. The method of claim 1 further comprising illuminating an area of the bone tissue via a light assembly coupled to the handle portion.

5. The method of claim 1 wherein the neural element threshold includes a proximity of the tip to the neural element.

* * * * *